(12) United States Patent
Panzenbeck et al.

(10) Patent No.: US 10,595,834 B2
(45) Date of Patent: Mar. 24, 2020

(54) SYSTEM AND METHODS FOR CONTROLLING STIFFNESS OF A NEEDLE OR CATHETER

(71) Applicant: Spiration, Inc., Redmond, WA (US)

(72) Inventors: Jason T. Panzenbeck, Seattle, WA (US); Michael S. Smith, Sammamish, WA (US)

(73) Assignee: Spiration, Inc., Redmond, WA (US)

( * ) Notice: Subject to any disclaimer, the term of this patent is extended or adjusted under 35 U.S.C. 154(b) by 175 days.

(21) Appl. No.: 15/856,459

(22) Filed: Dec. 28, 2017

(65) Prior Publication Data

US 2019/0200967 A1 Jul. 4, 2019

(51) Int. Cl.
*A61B 10/04* (2006.01)

(52) U.S. Cl.
CPC ........ *A61B 10/04* (2013.01); *A61B 2010/045* (2013.01)

(58) Field of Classification Search
CPC .............. A61B 10/04; A61B 2010/045; A61B 2010/0275; A61B 17/8819; A61M 25/0102

See application file for complete search history.

(56) References Cited

U.S. PATENT DOCUMENTS

2016/0331878 A1* 11/2016 McGillicuddy ...... A61B 10/025

* cited by examiner

*Primary Examiner* — Jocelin C Tanner

(57) ABSTRACT

A needle system includes a needle, a needle handle coupled to a proximal end of the needle and a needle stiffening device. The needle stiffening device includes a first handle portion, a second handle portion, a stylet having a distal end component and a shaft component, a fixing component configured to fix a proximal end of the stylet to the first handle portion, a hollow component configured to slidably receive the shaft component of the stylet and a compression device having a proximal end that makes contact with a distal end of the hollow component and a distal end that makes contact with the distal end component of the stylet. A distal end of the second handle portion makes contact with a proximal end of the hollow component within the first handle portion.

16 Claims, 5 Drawing Sheets

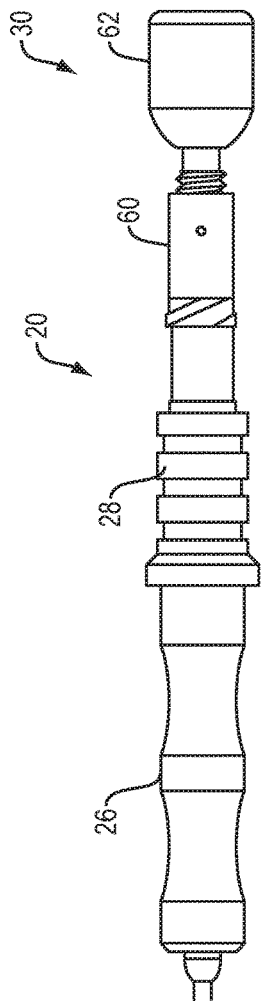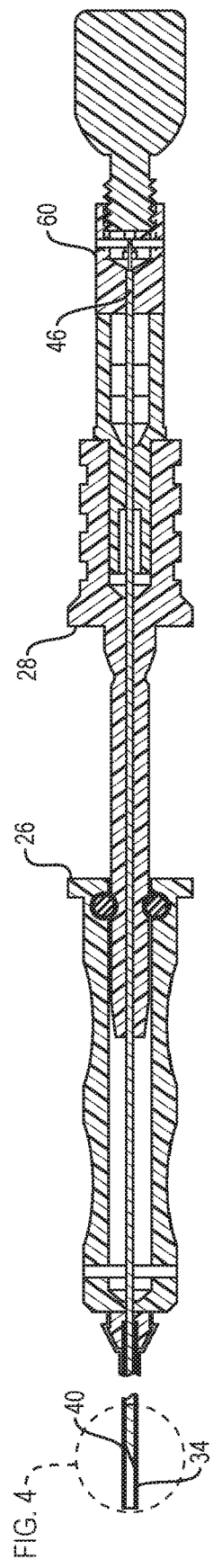
FIG. 1-1.
FIG. 1-2.

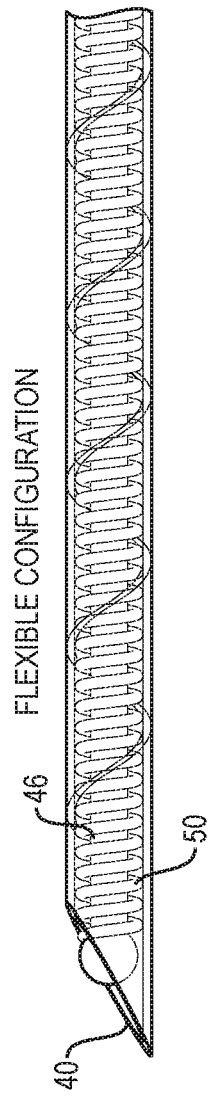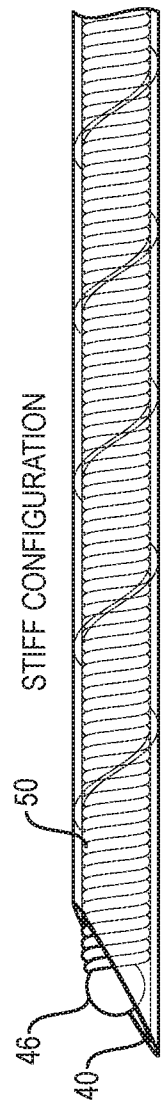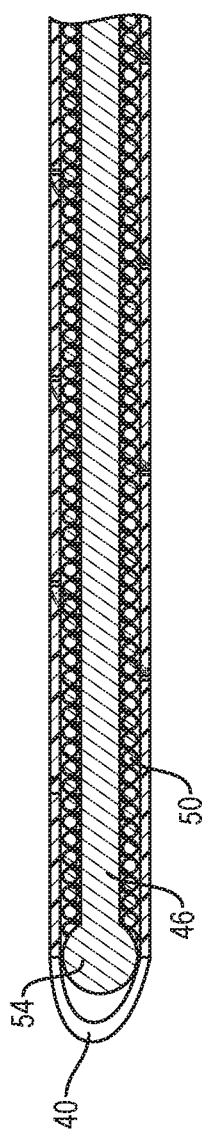

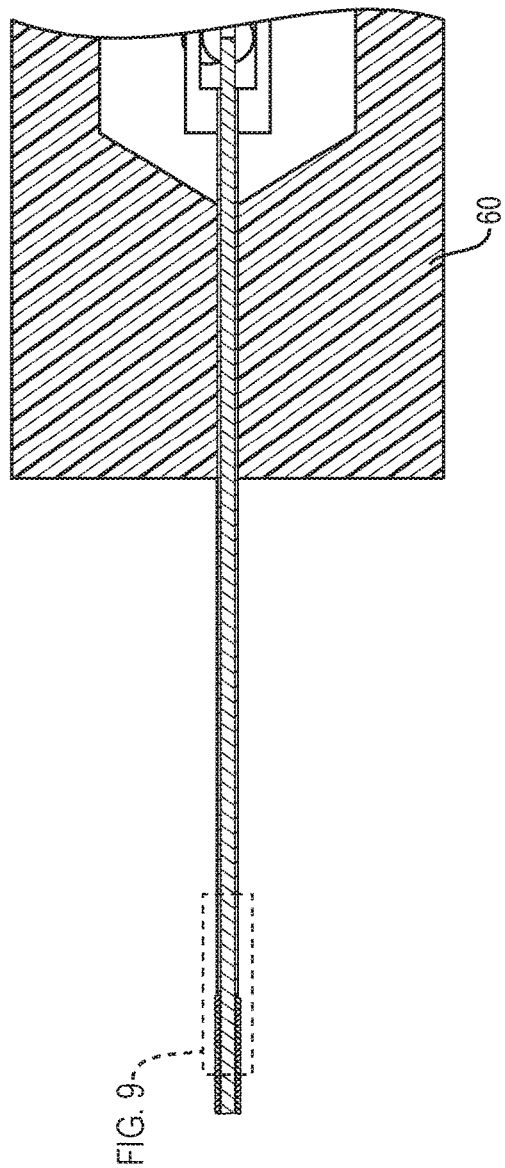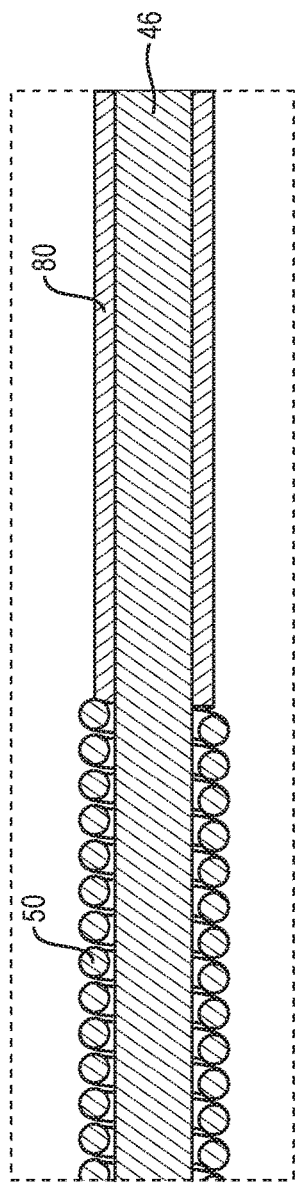

SYSTEM AND METHODS FOR CONTROLLING STIFFNESS OF A NEEDLE OR CATHETER

BACKGROUND

In recent years, a bronchoscope has widely been used in which an elongated insertion part is inserted into a body cavity, to thereby observe an inspection objective part within the body cavity without the necessity of incision or excision and, under certain circumstances, to thereby use a treatment tool, e.g., needle, so as to be able one to perform therapy and treatment.

The insertion part of the bronchoscope is so arranged as to have flexibility so as to be capable of being inserted into a bent or curved insertion path. Because the insertion part of the bronchoscope can have arduous curves used within the airways, the treatment tool, such as a needle, needs to have equal flexibility. However, if the treatment tool is too flexible, it may be ineffective when exposed outside of the insertion part of the bronchoscope. But, a needle flexible enough to navigate the arduous curves may not have enough translational stiffness for sampling.

SUMMARY

The present invention provides a needle system that includes a needle, a needle handle coupled to a proximal end of the needle and a needle stiffening device. The needle stiffening device includes a first handle portion, a second handle portion, a stylet having a distal end component and a shaft component, a fixing component configured to fix a proximal end of the stylet to the first handle portion, a hollow component configured to slidably receive the shaft component of the stylet and a compression device having a proximal end that makes contact with a distal end of the hollow component and a distal end that makes contact with the distal end component of the stylet. A distal end of the second handle portion makes contact with a proximal end of the hollow component within the first handle portion.

In one aspect of the invention, longitudinal movement of the second handle portion relative to the first handle portion in the distal direction causes the hollow component to apply a distal force to the compression device. The compression device includes a spring.

In another aspect of the invention, the first handle portion includes a partially threaded cavity and the second handle portion includes a threaded shaft configured to be received by the partially threaded cavity of the first handle portion.

In still another aspect of the invention, the fixing component includes at least one of a pin or a set screw.

In yet another aspect of the invention, the system further includes a link component configured to maintain contact with the hollow component and the second handle portion. Longitudinal motion of the link component does not affect the position of the fixing component and the stylet relative to the first handle portion.

In further aspects of the invention, a distal surface of the first handle portion makes contact with a proximal surface of the needle handle.

In still further aspects of the invention, a distal end of the first handle portion attaches to a proximal end of the needle handle.

Further features, advantages, and areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1-1 shows a side view of a controllable-stiffness needle device formed in accordance with an embodiment of the present invention;

FIG. 1-2 shows a top, cross-sectional view of the device shown in FIG. 1-1;

FIG. 2 shows a partial x-ray view of a distal end of the device shown in FIG. 1-1 in a flexible configuration;

FIG. 3 shows a partial x-ray view of the distal end of the device shown in FIG. 1-1 in a stiffer configuration than the flexible configuration shown in FIG. 2;

FIG. 4 shows a top, cross-sectional view of the distal end of the device shown in FIG. 3;

FIG. 6-1 shows a cross-sectional view of the handle shown in FIG. 5;

FIG. 6-2 shows a second cross-sectional view of the handle shown in FIG. 5;

FIG. 7-1 illustrates a detailed view of a portion of the handle shown in FIG. 5 in a first compressed configuration;

FIG. 7-2 illustrates a detailed view of a portion of the handle shown in FIG. 5 in a second compressed configuration;

FIG. 8 shows a side cross-sectional view of a portion of the stylet system; and

FIG. 9 shows a detailed cross-sectional view of a central portion of the stylet system.

DETAILED DESCRIPTION

The present invention provides a system for altering the stiffness of a flexible tube, such as a needle or a catheter.

Figures 2, 6:
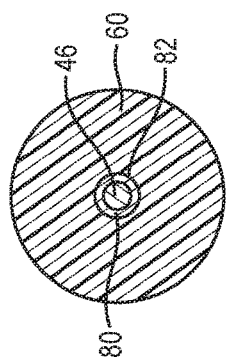
Figures 1, 6:
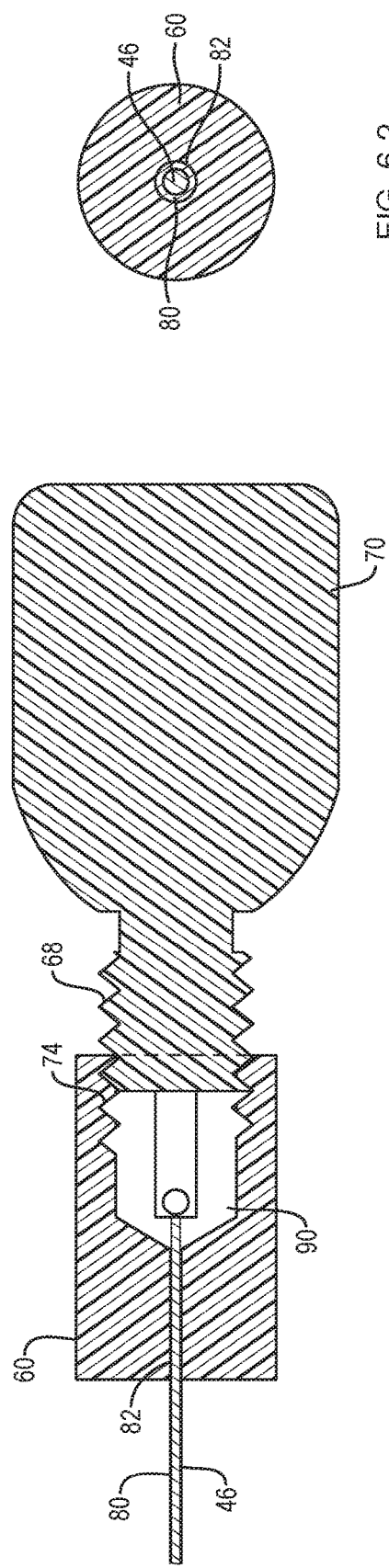

FIGS. 1-1 and the 1-2 show an example needle system 20 that includes a sheath handle portion 26 connected to a sheath 34, a needle handle portion 28 connected to a needle 40 and a stylet stiffening system having a handle 30 that is coupled to a stylet 46. The needle handle portion 28 allows a user to extend the needle 40 from a distal end of the sheath 34 in order to acquire tissue samples for example. The needle system 20 is receivable within a scope device, such as a bronchoscope or an endoscope.

The portion of the scope device that is within the body lumen may experience many arduous curves in order to follow the path of the body lumen. For example, the scope device is a bronchoscope and is received within airways of a lung. The more peripherally the bronchoscope is advanced into the lung the more arduous curves that the insertion tube of the bronchoscope will experience. The needle 40 is flexible so that needle failure does not occur as the needle 40 and the sheath 34 are passed through the arduous curves of the insertion tube. The needle 40 may include various flexibility features, such as an etched patterns or grooves in a metal.

The stylet stiffening device handle 30 includes a stylet handle portion 60 and a stiffening knob 62. By changing the position of the stiffening knob 62 relative to the stylet handle portion 60, the stiffness of the stylet 46 is altered between a flexible state and a stiffer state. The stylet 46 is received within the needle 40. As such, the stiffness of the needle 40 is altered due to the changing stiffness of the components mounted on the stylet 46.

As shown in FIGS. 2 through 4, the stylet stiffening system includes the stylet 46 and a spring-like device 50 located at least at a distal end of the stylet stiffening system. The stylet 46 includes a bulb or stopper 54 located at its distal end with a shaft connecting the stopper 54 to the stylet handle portion 60. The stopper 54 has a cross-sectional value that is larger than a cross-sectional value of the shaft that is located within the spring-like device 50.

The spring-like device 50 may be a spring or other compressible device formed of any of a number of different types of metals, polymers or the like that has at least a portion that can be compressed along a longitudinal axis. As shown in FIGS. 3 and 4, the spring-like device 50 is in a compressed or stiff configuration. As shown in FIG. 2, the spring-like device 50 is in a flexible configuration or a configuration that is less stiff than the spring-like device 50 shown in FIG. 3. Compression and decompression of the spring-like device 50 be described in more detail below.

Figure 5:
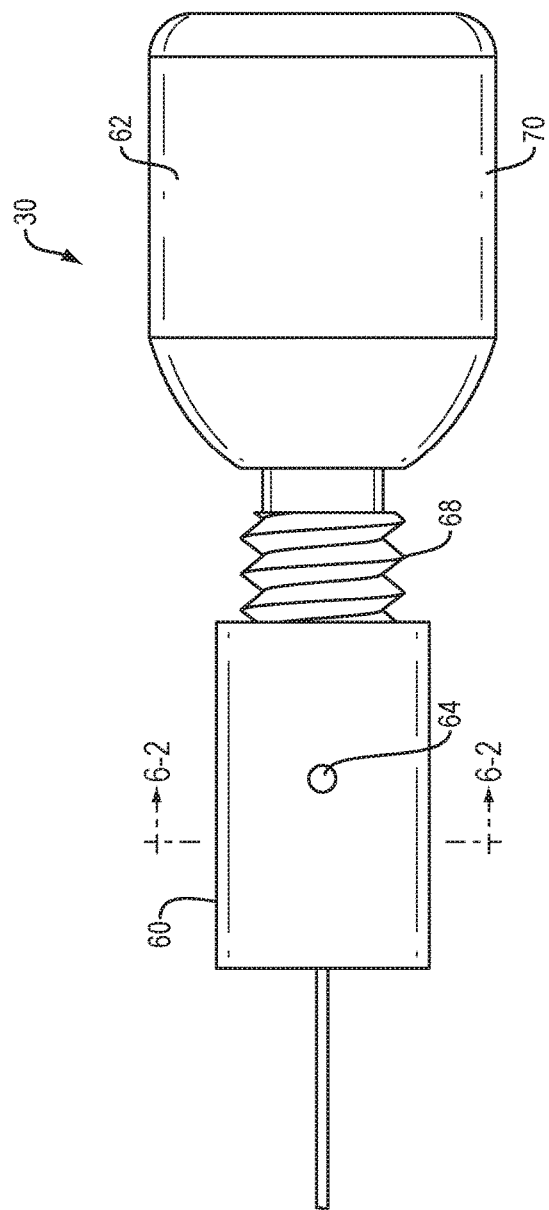
FIG. 5 shows a side view of a handle of a stylet system included in the device shown in FIGS. 1 through 4.
Figures 1, 7:
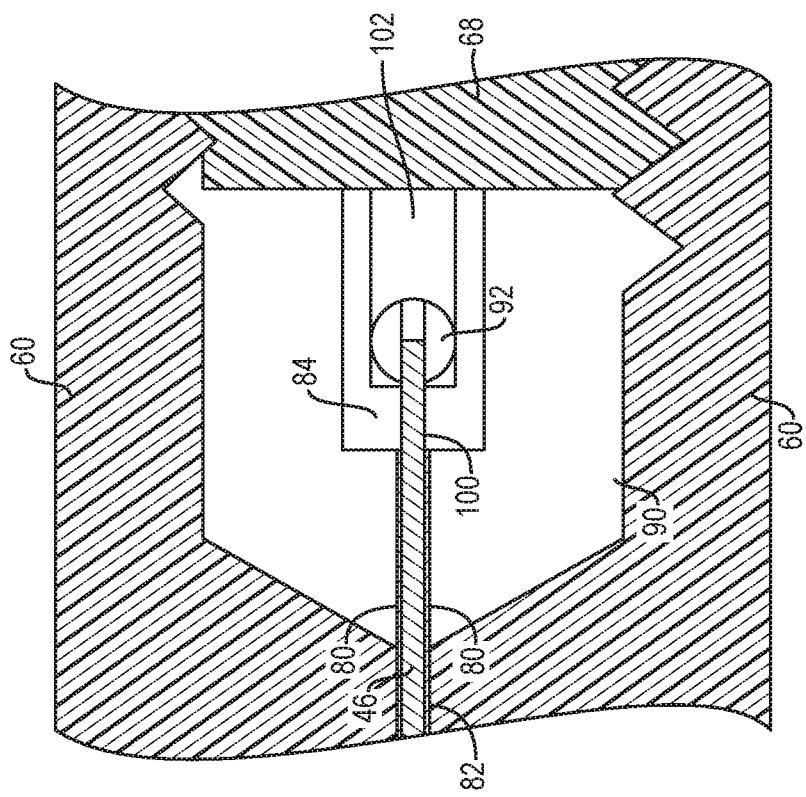
Figures 2, 7:
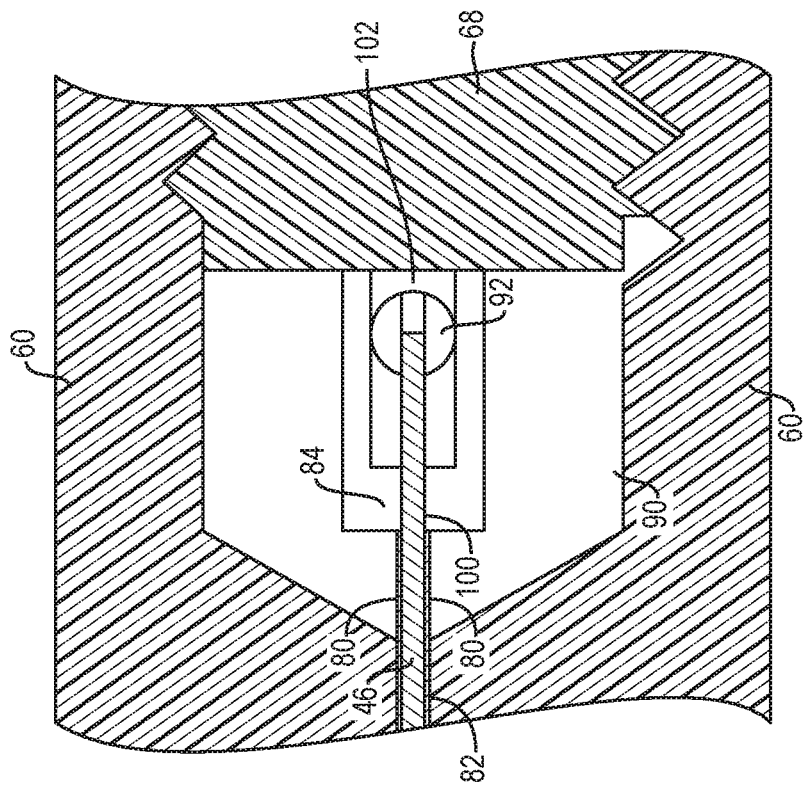

As shown in FIGS. 5-7, the stiffening knob 62 includes an externally threaded shaft 68 at its distal end and a knob 70 at its proximal end. The stylet handle portion 60 includes a first passageway 82 and a second passageway 90. The first passageway 82 connects a distal end of the second passageway 90 to the environment adjacent to a distal surface of the stylet handle portion 60. The second passageway 90 connects a proximal end of the first passageway 82 to the environment adjacent to a proximal side of the stylet handle portion 60. The first passageway 82 is sized to slidably receive the stylet 46 and a compressing tube 80, see FIG. 6-2. The second passageway 90 has a larger cross-sectional value than a cross-sectional value of the first passageway 82. The second passageway 90 includes an internal threaded wall 74 that extends from the proximal end of the stylet handle portion 60 to a predefined distance within the second passageway 90. The internal threaded wall 74 is configured to receive the externally threaded shaft 68 of the stiffening knob 62. In an alternate embodiment, the threaded components are not included and the configuration between the stiffening knob 62 and the stylet handle portion 60 is friction-based to allow the stiffening knob 62 to change positions longitudinally but remain in place until further activation by an outside force (e.g., a user).

As shown in FIG. 7, a stylet anchoring device 92 connects to a proximal end of the stylet 46 and a housing portion of the stylet handle portion 60. The stylet anchoring device 92 keeps the stylet 46 in a longitudinal position relative to the stylet handle portion 60. Thus, when the distal surface of the stylet handle portion 60 is placed in contact with or secured to a proximal end of the needle handle portion 28, the stopper 54 maintains its position longitudinally with regard to the needle 40.

The stylet stiffening system also includes a link component 84 that is slidably positioned within the second passageway 90. The link component 84 includes a first passageway 100 and a second passageway 102. The first passageway 100 connects a distal end of the second passageway 102 to the environment adjacent to a distal surface of the link component 84. The second passageway 102 connects between a proximal end of the first passageway 100 and the distal surface of the externally threaded shaft 68. The first passageway 100 is sized to slidably receive the stylet 46 but not the compressing tube 80. The second passageway 102 has a larger cross-sectional value than a cross-sectional value of the first passageway 100. The second passageway 102 is sized to slide longitudinally around the stylet anchoring device 92. Thus, as the externally threaded shaft 68 is advanced distally within the second passageway 90 of the stylet handle portion 60, the distal end of the externally threaded shaft 68 pushes the link component 84 distally which thus pushes the compressing tube 80 distally as well. The link component 84 may be fixed to the shaft 68 and/or the compressing tube 80. Any components directly or indirectly attached to the shaft 68 will rotate, if rotation is required to move the shaft 68 longitudinally within the stylet handle portion 60. The relationship between all the components allows a user to vary the stiffness of the stylet 46 and thus the needle 40 from a stiff mode (i.e., fully compressed spring-like device 50) to a flexible mode (i.e., relaxed spring-like device 50).

The stylet anchoring device 92 provides a mechanical connection between the stylet 46 and the stylet handle portion 60. For example, the stylet anchoring device 92 may be a set screw, a pin or other comparable connection device. In one embodiment, the stylet 46 includes an indent for receiving the stylet anchoring device 92 or the stylet 46 has a greater width value than the stylet anchoring device 92 and the stylet 46 includes a hole for receiving the stylet anchoring device 92. In one embodiment, an adhesive attaches the proximal end of the stylet 46 to the stylet anchoring device 92.

As shown in FIGS. 8 and 9, a proximal end of the spring-like device 50 maintains contact with a distal end of the compressing tube 80 due to biasing of the spring-like device 50. As the stiffening knob 62 is advanced within the stylet handle portion 60, the spring-like device 50 is compressed by the distal motion of the compressing tube 80. Compression of the spring-like device 50 causes the stylet to act in a stiffer manner, thus causing the needle 42 to also act in a stiffer manner. As the stiffening knob 62 is retracted proximally relative to the stylet handle portion 60, the spring-like device 50 becomes less compressed by the proximal motion of the compressing tube 80. Decompression of the spring-like device 50 causes the stylet to act in a more flexible manner, thus causing the needle 42 to also act in a more flexible manner.

A. A device comprising: a first handle portion; a second handle portion; a stylet comprising: a distal end component; and a shaft component coupled to the distal end component; a fixing component configured to restrict longitudinal motion of the stylet relative to the first handle portion; a hollow component configured to slidably receive at least a portion of the shaft component of the stylet; and a compression device comprising a proximal end that makes contact with a distal end of the hollow component and a distal end that makes contact with the distal end component of the stylet, wherein a distal end of the second handle portion makes contact with a proximal end of the hollow component within the first handle portion.

B. The device of A, wherein longitudinal movement of the second handle portion relative to the first handle portion in the distal direction causes the hollow component to apply a distal force to the compression device.

C. The device of any of A or B, wherein the compression device comprises a spring.

D. The device of any of A-C, wherein the first handle portion comprises a partially threaded cavity, wherein the second handle portion comprises a threaded shaft configured to be received by the partially threaded cavity of the first handle portion.

E. The device of any of A-D, wherein the fixing component comprises at least one of a pin or a set screw.

F. The device of any of A-E, further comprising a link component configured to maintain contact with the hollow component and the second handle portion.

G. The device of F, wherein longitudinal motion of the link component does not affect the position of the fixing component and the stylet relative to the first handle portion.

H. A needle system comprising: a needle; a needle handle coupled to a proximal end of the needle; and a needle stiffening device comprising: a first handle portion; a second handle portion; a stylet configured to be received within the needle, the stylet comprising: a distal end component; and a shaft component coupled to the distal end component; a fixing component configured to fix a proximal end of the stylet to the first handle portion; a hollow component configured to slidably receive the shaft component of the stylet; and a compression device comprising a proximal end that makes contact with a distal end of the hollow component and a distal end that makes contact with the distal end component of the stylet, wherein a distal end of the second handle portion makes contact with a proximal end of the hollow component within the first handle portion.

I. The system of H, wherein longitudinal movement of the second handle portion relative to the first handle portion in the distal direction causes the hollow component to apply a distal force to the compression device.

J. The system of H or I, wherein the compression device comprises a spring.

K. The system of any of H-J, wherein the first handle portion comprises a partially threaded cavity, wherein the second handle portion comprises a threaded shaft configured to be received by the partially threaded cavity of the first handle portion.

L. The system of any of H-K, wherein the fixing component comprises at least one of a pin or a set screw.

M. The system of any of H-L, further comprising a link component configured to maintain contact with the hollow component and the second handle portion.

N. The system of M, wherein longitudinal motion of the link component does not affect the position of the fixing component and the stylet relative to the first handle portion.

O. The system of any of H-N, wherein a distal surface of the first handle portion makes contact with a proximal surface of the needle handle.

P. The system of H-O, wherein a distal end of the first handle portion attaches to a proximal end of the needle handle.

The description of the invention is merely exemplary in nature and variations that do not depart from the gist of the invention are intended to be within the scope of the invention. Such variations are not to be regarded as a departure from the spirit and scope of the invention.

Although the preferable embodiments of the present invention have been described hitherto, the present invention is not limited to these embodiments. Additions, omissions, substitutions, and other modifications can be made without departing from the spirit or scope of the present invention.

In addition, the invention is not limited by the above description and is limited by only the scope of appended claims.

What is claimed is:

1. A device comprising:
a first handle portion comprising a cavity with a distal port and a proximal port;
a second handle portion configured to be at least partially received within the cavity of the first handle portion via the proximal port;
a stylet at least partially received within the cavity via the distal port, the stylet comprising:
a distal end component; and
a shaft component coupled to the distal end component;
a fixing device configured to restrict longitudinal motion of the stylet relative to the first handle portion, the fixing device is in contact with the first handle portion;
a hollow component configured to slidably receive at least a portion of the shaft component of the stylet; and
a compression device comprising:
a proximal end that makes contact with a distal end of the hollow component within the cavity;
a distal end that makes contact with the distal end component of the stylet; and
a lumen configured to slidably receive the shaft component of the stylet,
wherein a distal end of the second handle portion makes contact with a proximal end of the hollow component within the cavity of the first handle portion;
wherein the hollow component is located between the second handle portion and the compression device.

2. The device of claim 1, wherein longitudinal movement of the second handle portion relative to the first handle portion in the distal direction causes the hollow component to apply a distal force to the compression device.

3. The device of claim 1, wherein the compression device comprises at least one of a spring or an elastic member.

4. The device of claim 1, wherein the proximal port of the first handle portion is at least partially threaded, wherein the second handle portion comprises a threaded shaft configured to be received by the partially threaded proximal port of the first handle portion.

5. The device of claim 1, wherein the fixing device comprises at least one of a pin or a set screw.

6. The device of claim 1, further comprising a link component configured to maintain contact with the hollow component and the second handle portion.

7. The device of claim 6, wherein longitudinal motion of the link component does not affect the position of the fixing device and the stylet relative to the first handle portion.

8. A needle system comprising:
a needle comprising a lumen;
a needle handle coupled to a proximal end of the needle, the needle handle comprising a port configured to provide access to the lumen of the needle; and
a needle stiffening device comprising:
a first handle portion comprising a cavity with a distal port and a proximal port;
a second handle portion configured to be at least partially received within the cavity of the first handle portion via the proximal port;
a stylet at least partially received within the cavity via the distal port, the stylet configured to be received within the lumen of the needle via port of the needle handle, the stylet comprising:
a distal end component; and
a shaft component coupled to the distal end component;
a fixing device configured to fix a proximal end of the stylet to the first handle portion, the fixing device is in contact with the first handle portion;
a hollow component configured to slidably receive the shaft component of the stylet; and
a compression device comprising:
a proximal end that makes contact with a distal end of the hollow component within the cavity;
a distal end that makes contact with the distal end component of the stylet; and
a lumen configured to slidably receive the stylet, wherein a distal end of the second handle portion makes contact with a proximal end of the hollow component within the cavity of the first handle portion, wherein the hollow component is located between the second handle portion and the compression device.

9. The system of claim 8, wherein longitudinal movement of the second handle portion relative to the first handle portion in the distal direction causes the hollow component to apply a distal force to the compression device.

10. The system of claim 8, wherein the compression device comprises a spring.

11. The system of claim 8, wherein the proximal port of the first handle portion is at least partially threaded, wherein the second handle portion comprises a threaded shaft configured to be received by the partially threaded proximal port of the first handle portion.

12. The system of claim 8, wherein the fixing device comprises at least one of a pin or a set screw.

13. The system of claim 8, further comprising a link component configured to maintain contact with the hollow component and the second handle portion.

14. The system of claim 13, wherein longitudinal motion of the link component does not affect the position of the fixing device and the stylet relative to the first handle portion.

15. The system of claim 8, wherein a distal surface of the first handle portion makes contact with a proximal surface of the needle handle.

16. The system of claim 8, wherein a distal end of the first handle portion attaches to a proximal end of the needle handle.

\* \* \* \* \*